United States Patent
Storet

(10) Patent No.: US 6,458,987 B1
(45) Date of Patent: Oct. 1, 2002

(54) CITRONELLYL AND/OR DIHYDROCITRONELLYL LACTATES, THEIR PREPARATION AND THEIR USE

(75) Inventor: Isabelle Storet, Les Eparres (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/582,902
(22) PCT Filed: May 18, 1999
(86) PCT No.: PCT/FR99/01181
§ 371 (c)(1), (2), (4) Date: Jul. 6, 2000
(87) PCT Pub. No.: WO99/59955
PCT Pub. Date: Nov. 25, 1999

(30) Foreign Application Priority Data

May 20, 1998 (FR) .............................................. 98/06403

(51) Int. Cl.$^7$ ............................................... C07C 69/66
(52) U.S. Cl. .......................................... 560/179; 512/26
(58) Field of Search ................................. 560/174, 179; 562/26; 512/26

(56) References Cited

U.S. PATENT DOCUMENTS 3,402,721 A    9/1968    Theimer ....................... 131/17

OTHER PUBLICATIONS

Database Crossfire 'Online' Beilstyein information system GMBH, Frankfurt, DE—BRN=1712865, XP002091755 abstract & Sabatay: Bulletin De La Societe Chimique de France, vol. 47 No. 4, p. 436 Paris, FR.
International Search Report.

Primary Examiner—Gary Geist
Assistant Examiner—Paul A. Zucker

(57) ABSTRACT

The invention concerns novel chemical compounds, namely citronellyl lactate and dihydrocitronellyl lactate and their optically active forms. The invention also concerns the method for obtaining them. The invention further concerns their use in the field of perfumes.

24 Claims, 2 Drawing Sheets

CITRONELLYL AND/OR DIHYDROCITRONELLYL LACTATES, THEIR PREPARATION AND THEIR USE

This application is an application under 35 U.S.C. Section 371 of International Application Number PCT/FR99/01181 filed on May 18, 1999.

A subject of the present invention is new chemical compounds, namely citronellyl lactate and dihydrocitronellyl lactate and their optically active forms.

The invention also relates to a process for obtaining them.

The present invention relates in particular to their use in the field of perfumery. The said compounds have interesting olfactory properties and can be used, inter alia, for the preparation of perfuming compositions and perfumed products.

The perfumery industry is constantly seeking products which, through the originality, volume and power of their fragrance, confer a quite special character upon the compositions in which they feature.

The literature contains very little information about the use of lactic esters in perfumery.

It has now been found that citronellyl lactate and dihydrocitronellyl lactate and their optically active forms defined below displayed original olfactory properties.

It is to be noted that it is impossible for a person skilled in the art to foresee whether a given chemical compound will or will not possess a smell that is interesting from the olfactory point of view and what its character will be.

A subject of the invention is thus new esters of lactic acid, citronellyl lactate and dihydrocitronellyl lactate conforming respectively to formulae (I) and (I'):

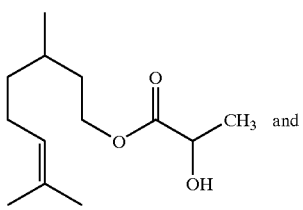

(I)

and

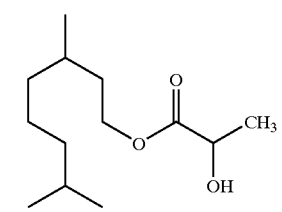

(I')

The invention also relates to the optically active (R) and (S) forms conforming to formula (Ia) and (I'a):

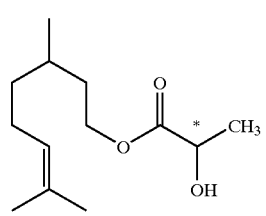

(Ia)

and

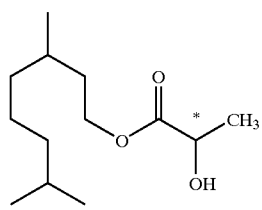

(I'a)

In the formulae (Ia) and (I'a), the optically active carbon atom taken into consideration is the carbon atom in a position of the $CH_3$ group and of the ester function.

It has been found that, depending on the form of the said lactates, that is to say according to whether they were in racemic form or in a pure optically active form, they presented a different smell.

Thus, the (R)-citronellyl lactate exhales a flowery character of lily of the valley type, warm and rich and more natural than rosy alcohols, whereas the (S)-citronellyl lactate displays a flowery honeysuckle character closer to citronellol, which gives it a less natural effect than the (R)-citronellyl lactate.

As regards the racemic mixture, the smell of the citronellyl lactate has a flowery character of lily of the valley/honeysuckle type which is less powerful and less natural than the (R)-citronellyl lactate.

As far as the (R)-dihydrocitronellyl lactate is concerned, it has a citronella-like, grassy, woody character, whereas that of the (S)-dihydrocitronellyl lactate is of the rosy, woody and lemony type.

Figure 1:
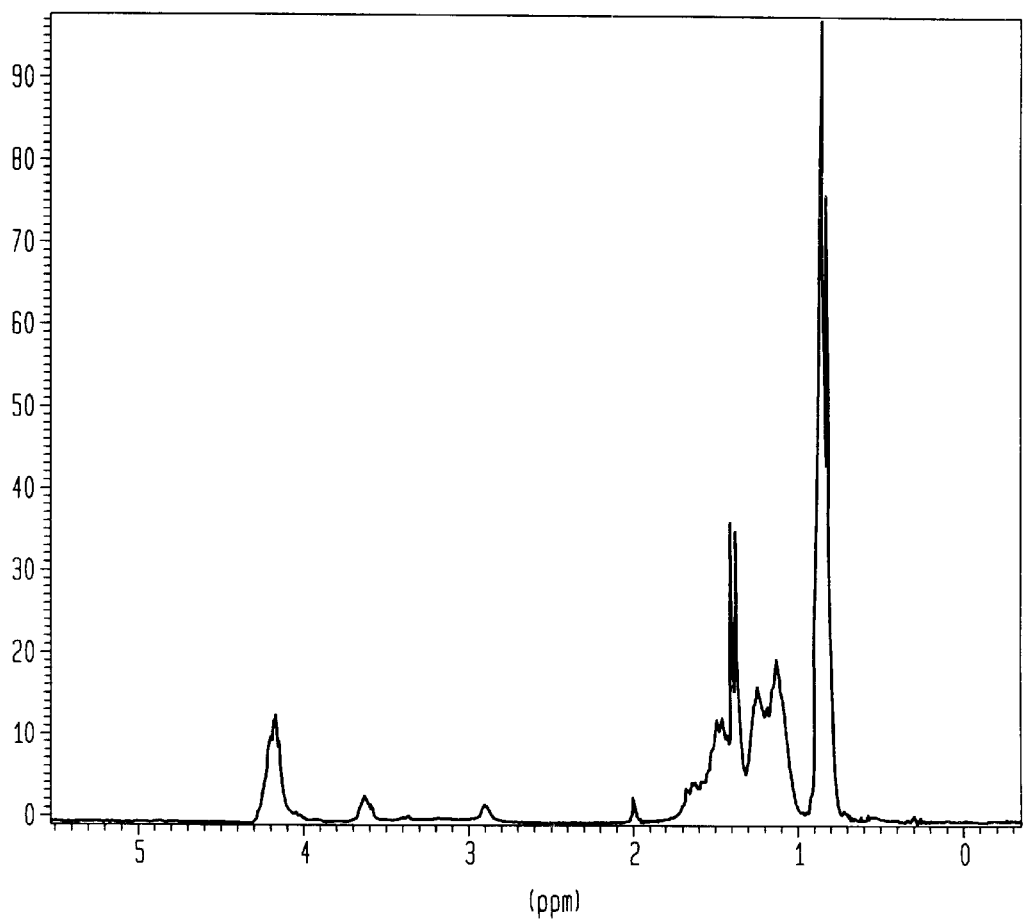
FIG. 1 is a $NMR^1H$ spectrum of (R)-dihydrocitronellyl lactate.

The compounds of formula (I) and (I') and their optically active forms (Ia) and (I'a) can be prepared by different preparation methods.

One of the access routes to the compounds of formula (I) and/or (I') comprises the reacting of:

lactic acid, its salts or esters of formula (II):

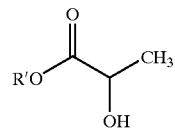

(II)

in formula (II), R' represents a hydrogen atom, an alkali-metal atom, an ammonium radical or an alkyl radical, linear or branched having from 1 to 4 carbon atoms, and the citronellol of formula (III) and/or the dihydrocitronellol of formula (III'):

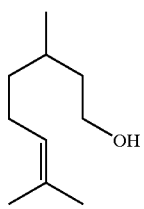

(III)

and

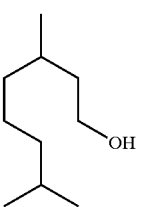

(III')

As regards the preparation of the optically active compounds conforming to formula (Ia) and (I'a), they can be obtained by the reacting of:

lactic acid, its optically active salts or esters of formula (IIa):

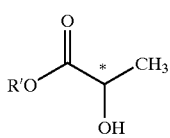

(IIa)

in formula (IIa), R' represents a hydrogen atom, an alkali-metal atom, an ammonium radical or an alkyl radical, linear or branched having from 1 to 4 carbon atoms, and the citronellol of formula (III) and/or the dihydrocitronellol of formula (III'):

According to the process of the invention, the lactic acid or its derivatives are reacted with the citronellol or the dihydrocitronellol.

As regards the compounds of formula (II) or (IIa), use is made more particularly of lactic acid, sodium or potassium lactate, or of the methyl or ethyl esters of lactic acid.

To prepare an optically active lactic ester (Ia) or (I'a), the starting point is the optical isomer of formula (IIa) having the desired (R) or (S) configuration, in the knowledge that the reaction allows the preservation of the stereochemistry of the original isomer.

The (R)-lactic acid or its derivatives are used for preference.

A compound of formula (IIa) having a good optical purity, generally less than 10% of the other enantiomer, preferably less than 5%, and even more preferably less than 3%, even down to 0%, is chosen for preference.

Compounds of formula (IIa) meeting the aforementioned requirements are found in the trade.

Thus, the commercial lactic acid which is generally found in the form of a 85% aqueous solution can be used.

As regards the alcohol, an alcohol is used which has a good chemical purity preferably exceeding 85%.

Depending on the form of the compound of formula (I), (I') or (Ia), (I'a), several modes of preparation can be considered.

A first reaction comprises the reacting of the lactic acid with the citronellol and/or the dihydrocitronellol. It is also possible to carry out the esterification in the presence of an organic solvent. The organic solvent is chosen in such a way that it forms an azeotrope with the water and the boiling point of its azeotrope with the water is lower than that of the alcohol involved. Examples of solvents that can be cited in particular are toluene, cumene or pseudocumene.

A second variant is to react the lactic acid or its salts in an activated and protected form with the citronellol and/or the dihydrocitronellol. Thus, the lactic acid or its salts are first reacted with phosgene, diphosgene (trichloromethylchloroformate) or thionyl chloride in order to obtain, respectively, dioxolan-1,3 dione-2,4-methyl-5 or propene-one-1 sulphite-1,2 with which the citronellol and/or the dihydrocitronellol is reacted. The quantity of phosgene, of diphosgene or of thionyl chloride used is generally equal to the stoichiometric quantity.

A third variant is to carry out the reaction of the lactic acid in ester form with the citronellol and/or the dihydrocitronellol, then distill of the corresponding alcohol liberated by transesterification.

The different reactions are carried out in the presence of a standard acid-type catalyst. There may be cited in particular sulphuric acid, sulphonic p-toluene acid, antimony oxide, alkyl or aryl titanates such as the titanates of methyl, ethyl, n-propyl, isopropyl, t-butyl, cyclohexyl, phenyl, tolyl; monoethanolamine titanate, diethanolamine titanate, triethanolamine titanate.

Sodium methylate or potassium methylate can also be used.

The quantity of the reagents present is determined in such a way that the molar ratio between the lactic acid and the citronellol and/or the dihydrocitronellol varies between 0.5 and 5, and preferably between 1 and 3.

The quantity of catalyst used, expressed relative to the weight of the lactic acid or derivative, is advantageously chosen between 0.1 and 5%.

When an organic solvent is present, the quantity used can vary greatly. By way of indication, it can be stated that the quantity of organic solvent can represent from 50 to 200% of the weight of the lactic acid used.

The temperature of the reaction is chosen so that it is sufficient to allow the completion of the reaction and the distillation of the liberated alcohol if necessary.

The temperature of the reaction is preferably chosen between 50 and 150° C.

The reaction is advantageously carried out under reduced pressure advantageously between 5 and 500 mbar.

The reaction is preferably carried out under atmosphere of an inert gas which can be nitrogen or a rare gas, preferably argon.

From a practical point of view, the procedure according to the invention is simple to implement.

The different reagents can be introduced in any order. For preference, the following order of reagents is chosen: the lactic acid or derivative is introduced and the citronellol and/or the dihydrocitronellol, then the acid catalyst.

The reaction medium is raised to the desired temperature, while keeping the reaction medium under agitation.

During the reaction, there is formation of water or release of alcohol in the reaction medium. A preferred variant of the invention comprises their elimination form the reaction medium, as and when they form, by any known means, in particular by azeotropic distillation.

At the end of the reaction, the desired lactic ester, the citronellol and/or the dihydrocitronellol in excess and the catalyst are obtained.

The lactic ester which has formed can be recovered from the reaction medium, by any appropriate means.

Thus, in particular, a washing with water can be carried out followed by a neutralization with the help of a base.

The quantity of base, preferably soda, is such that the pH is between 6 and 8.

The organic phase is separated and fractionated by distillation.

Most often there is collection first of all of the excess of citronellol and/or the dihydrocitronellol then of the desired lactic ester which can be, according to the case, a racemic mixture of citronellyl lactate of formula (I) and/or of dihydrocitronellyl lactate of formula (I') or their optically active forms of formula (Ia) or (I'a) or possibly a mixture of optically active forms.

Thus, in the following description of the invention, the term "lactic ester" takes account of its different variants.

Another subject of the present invention has as its aim perfuming compositions, products and perfuming substances characterized by the fact that they contain, as active principle having an influence on the smell, an effective quantity of at least one lactic ester of formula (I), (I'), (Ia) and (I'a).

The esters of the lactic acid and of the citronellol are particularly interesting. As previously mentioned, the ester in (R) form exhales a flowery character of lily of the valley type, warm and rich, while the (S) form has a flowery honeysuckle character.

The different products of the invention can serve as a base for the honeysuckle, lily of the valley and gardenia characters.

The term "perfuming compositions" is used to describe mixtures of various ingredients such as solvents, solid or liquid supports, fixing agents, various odorizing compounds, etc . . . in which at least one lactic ester of the invention is incorporated, which mixtures are used to endow various types of finished products with the sought fragrance.

The bases for perfume constitute preferred examples of perfuming compositions in which at least one lactic ester of the invention can be advantageously used.

Toilet waters, after-shave lotions, perfumes, creams, soaps, bath or shower gels or deodorant or antiperspirant products, be they in the form 6 of sticks or lotions, constitute examples of substances or finished products in which the lactic ester of the invention contributes its original character.

They can also feature in shampoos and in hair products of any type.

They can also perfume talcs or powders of any nature.

They may also be suitable for ambient-air deodorants or any maintenance product.

Another example of compositions into which the said compounds can advantageously be introduced is represented by the customary detergent compositions. These compositions generally contain one or more of the following ingredients: anionic, cationic or amphoteric surfactants, bleaching agents, optical bluing agents, various fillers, anti-redeposition agents. The nature of these various components is not critical and the lactic ester of the invention can be added to any type of detergent composition. They can be introduced into textile softeners in liquid form or into compositions deposited on support, most often a non-woven fabric, intended for use in tumble dryers.

The level of lactic ester of the invention in the compositions according to the invention, expressed as a percentage by weight in the composition in question, depends on the nature of the said composition (base for perfume or toilet water for example) and on the power and the nature of the sought effect in the final product. It goes without saying that in a base for perfume the level of lactic ester of the invention can vary widely, for example more than 5% by weight and can reach 90% by weight whereas in a perfume, a toilet water or an after-shave lotion this level can be well below 50% by weight.

The level of lactic ester in detergent compositions, in particular domestic, or in soaps, can be of the order of 0.01 to 2%.

They may also be included in perfumed shampoos at the rate of 0.005 to 2% or to perfume any hair product.

Thus the lower limit of the level of lactic ester of the invention can be that which causes a perceptible change in the smell of the fragrance or in the character of the finished product. In some cases, this minimum level may be of the order of 0.001% by weight. Obviously, levels can be used which are not contained in the limits mentioned above without thereby exceeding the scope of the present invention.

The products of the invention are particularly advantageous because of their olfactory stability during their application.

Embodiments of the invention are given below.

EXAMPLE 1

156.34 g (1.5 mol) of (R)-methyl lactate, 78.62 g (0.5 mol) of citronellol and 0.6 g of butyl titanate are placed in a flask.

The reaction mixture is heated to 90° C. for 24 h under a nitrogen current and under reduced pressure (140 mbar) and the liberated methanol is drawn off.

The reaction medium is washed in 3×100 ml of a 10% by weight NaCl solution.

The organic phase is dried with magnesium sulphate.

The organic phase is distilled under reduced pressure (0.2 mbar) and 65.7 g of (R)-citronellyl lactate are collected between 115° C. and 118° C.

The (R)-citronellyl lactate is identified by $NMR^1H$ and $NMR^{13}C$ which shows the presence of two diastereoisomers (dia A and B) namely (R,R) and (R,S).

$NMR^1H$=(300.13 MHz; $CDCl_3$): 0.84 (d, J=6.5 Hz, 3H); 1.12 (m, 1H); 1.24 (m, 1H); 1.32 (d, J=6.8 Hz, 3H); 1.42 (m, 1H+1H); 1.51 (s, 3H); 1.59 (s, 3H); 1.63 (m, 1H); 1.90 (m, 2H); 2.87 (broad peak, 1H); 4.14 (m, 1H+2H); 4.99 (t, J=7.1 Hz).

$NMR^{13}C$=(75.47 MHz; $CDCl_3$): 16.8, 19.3 (dia A); 19.4 (dia B); 20.3, 25.3, 25.6, 29.3 (dia A); 29.5 (dia B); 35.3; 36.4 (dia A); 36.9 (dia B); 64.1; 66.7; 124.4; 131.4; 175.7.

The smell of the (R)-citronellyl lactate has a flowery character of lily of the valley type, warm and rich and more natural than rosy alcohols.

EXAMPLE 2

Example 1 is reproduced using the (S)-methyl lactate.

43.77 g of (S)-citronellyl lactate are recovered.

The smell of the (S)-citronellyl lactate has a flowery honeysuckle character closer to citronellol, which gives it a less natural effect than the (R)-citronellyl lactate.

EXAMPLE 3

Example 1 is reproduced using methyl lactate.

50 g of citronellyl lactate are recovered.

The smell of the citronellyl lactate has a flowery character of lily of the valley-honeysuckle type, less powerful and less natural than the (R)-citronellyl lactate.

EXAMPLE 4

Example 1 is reproduced using the (R)-methyl lactate and dihydrocitronellol.

The smell of the (R)-dihydrocitronellyl lactate has a citronella-like, grassy and woody character.

The (R)-dihydrocitronellyl lactate is identified by NMR$^1$H, the spectrum of which constitutes FIG. 1.

EXAMPLE 5

Example 1 is reproduced using the (S)-methyl lactate and dihydrocitronellol.

The smell of the (S)-dihydrocitronellyl lactate has a rosy, woody and lemony type character.

Figure 2:
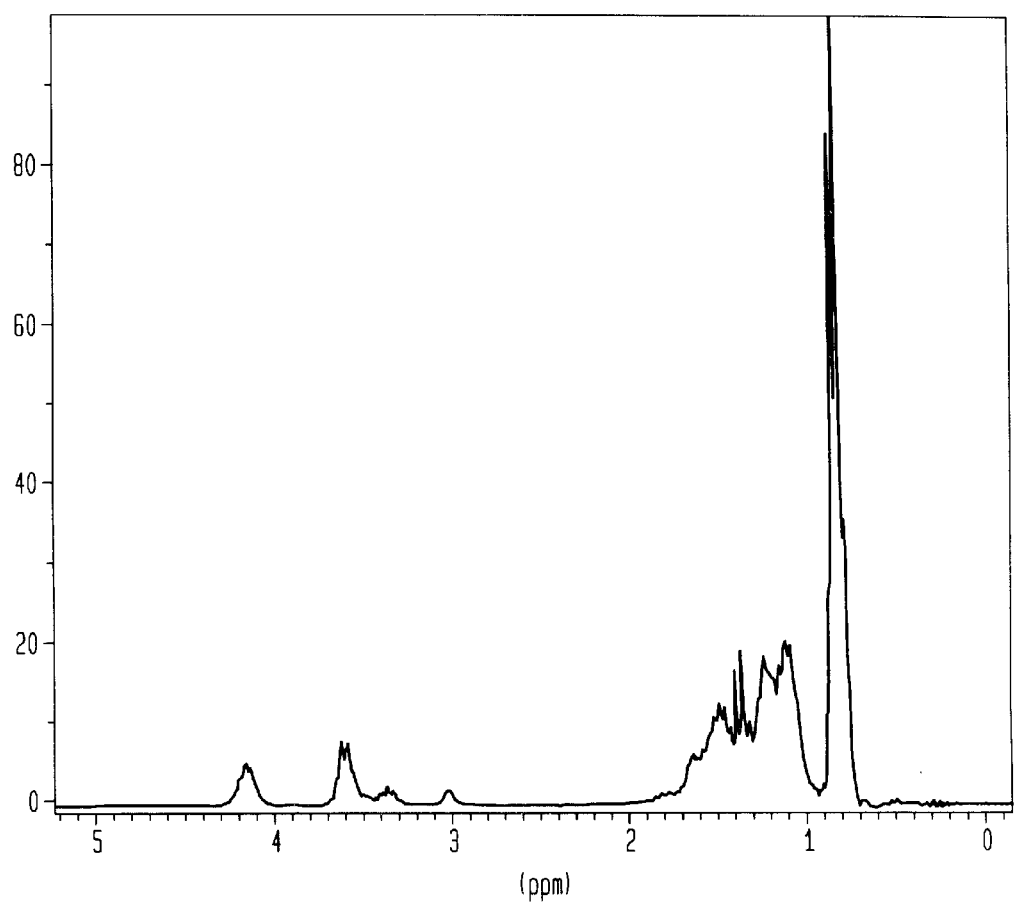
FIG. 2 is a $NMR^1H$ spectrum of (S)-dihydrocitronellyl lactate.

The (S)-dihydrocitronellyl lactate is identified by NMR$^1$H, the spectrum of which constitutes FIG. 2.

EXAMPLE 6

1.5 g of a 33% by weight solution of (R)-citronellyl lactate in polysorbate 20 (sorbitol ester) and fatty acids (lauric, stearic, oleic) ethoxylated by 20 E.O. are incorporated in 98.5 g of a shampoo base.

The shampoo has the following composition by weight:

| | |
|---|---|
| sodium lauryl sulphate + ethoxylated sodium lauryl sulphate + disodium cocoamphodiacetate + hexylene glycol (MIRACARE 2MCA S/E) | 30% |
| cocamidopropylamine oxide and lichen extract (ANTIPELLICULE USNATE AO) | 1% |
| Indian cress extract (CAPUCINE HS) | 1% |
| preservative (GERMABEN II) | 0.2% |
| citric acid | pH 6.0 to 6.2 |
| demineralized water | 67.3% |
| perfume | 0.5% |

The perfumed shampoo is stable in terms of colour and smell over a period of 3 months when it is stored at 50° C. sheltered from light and when it is stored at 20° C. in daylight.

EXAMPLE 7

1.5 g of a 33% by weight solution of (R)-citronellyl lactate in polysorbate 20 are incorporated in 98.5 g of a shower gel base.

The shower gel has the following composition by weight:

| | |
|---|---|
| ethoxylated sodium lauryl sulphate + sodium cocoamphoacetate + MIPA cocamide (MIRACARE CS) | 37.30% |
| HS wild camomile | 2.00% |
| hydroxypropylated guar (JAGUAR C162) | 0.30% |
| preservative (GERMABEN II E) | 0.20% |
| demineralized water | 59.7% |
| citric acid | pH 5.9 |
| perfume | 0.50% |

The perfumed shower gel is stable in terms of colour and smell over a period of 3 months when it is stored at 50° C. sheltered from light and when it is stored at 20° C. in daylight.

EXAMPLE 8

0.3 g of a 33% by weight solution of (R)-citronellyl lactate in polysorbate 20 are incorporated in 99.7 g of a hydrating gel base.

The hydrating gel has the following composition by weight:

| | |
|---|---|
| hydroxypropylated guar (JAGUAR HP 105) | 0.8% |
| hydroxylated guar + tri(hydroxypropyl)ammonium chloride (JAGUAR C162) | 0.2% |
| oleth 20 (RHODASURF ON 870) | 0.05% |
| allantoin | 0.2% |
| benzophenone 4 (UNIVUL MS 40) | 0.5% |
| glycerol | 0.25% |
| PCA sodium (NALIDONE) | 2.4% |
| citric acid | 2.0% |
| sodium hydroxide (10%) | pH 8 |
| DMDMH hydantoin (NIPA GUARD DMDMH) | 0.3% |
| perfume | 0.1% |
| polysorbate 20 (TWEEN 20) | 0.2% |
| deionized water | 93% |

The perfumed hydrating gel is stable in terms of colour and smell over a period of 3 months when it is stored at 50° C. sheltered from light and when it is stored at 20° C. in daylight.

EXAMPLE 9

0.3 g of (R)-citronellyl lactate is incorporated in 99.7 g of a hydrating cream base.

The hydrating cream base is prepared by mixing the following two phases having the following composition by weight:

| | |
|---|---|
| Phase A | |
| capryl/capric triglyceride (DERMOL M5) | 4% |
| mineral oil (MARCOL 82) | 2% |
| stearyl alcohol | 3% |
| isopropyl myristate (WICKENOL 111) | 2% |
| glyceryl stearate + polyethylene glycol 100 (ARLACEL 165) | 6% |
| dimethicone (MIRASIL DM 300) | 4% |
| Phase B | |
| deionized water | 70.7% |
| glycerol | 8% |
| preservative (GERMABEN II) | 0.3% |

The perfumed hydrating cream is stable in terms of colour and smell over a period of 3 months when it is stored at 50° C. sheltered from light and when it is stored at 20° C. in daylight.

EXAMPLE 10

0.2 g of (R)-citronellyl lactate is incorporated in 99.8 g of detergent powder.

The detergent powder has the following composition by weight:

| | |
|---|---|
| linear sodium alkylbenzene sulphonate (LABS NANSA) | 10% |
| SOAP | 5% |
| C12 ethoxylated alcohol, 70E (SINPERONIC A7) | 2% |
| sodium tripolyphosphate (RHODIAPHOS HPA 3.5) | 25% |
| sodium carbonate | 10% |
| sodium silicate R2 | 5% |
| sodium sulphate | % |
| sodium carboxymethylcellulose | 1% |
| sodium perborate | 15% |
| TAED | 5% |

-continued

| | |
|---|---|
| diethylenetriamine penta(methylene phosphonic acid) (DEQUEST 2066) | 1% |
| antifoaming agent (RHODORSIL 20448) | 1% |
| optical bluing agent (TINOPAL DMS) | 0.2% |

The perfumed detergent powder is stable in terms of colour and smell over a period of 3 months when it is stored at 50° C. sheltered from light and when it is stored at 20° C. in daylight.

EXAMPLE 11

| | |
|---|---|
| A perfuming composition is prepared containing: | |
| methyl dihydrojasmonate | 10 g |
| phenylethyl alcohol | 15 g |
| indole in 10% solution in DEP | 0.5 g of solution |
| benzyl acetate | 2.5 g |
| MAYOL (1-hydroxymethyl-4-isopropylcyclohexane) | 5 g |
| 4-(4-hydroxy-4-methylpentyl)-3-cyclohexene-1-carboxaldehyde (LYRAL) | 4.5 g |
| p-tert-butyl-methylhydrocinammaldehyde (LILIAL) | 5 g |
| (R)-citronellyl lactate | 7.5 g |

The use of (R)-citronellyl lactate permits the reconstitution of a lily of the valley base, which procures a much more natural effect than the base which does not contain any of it.

What is claimed is:

1. Citronellyl or dihydrocitronellyl lactates of formula (I) or (I'):

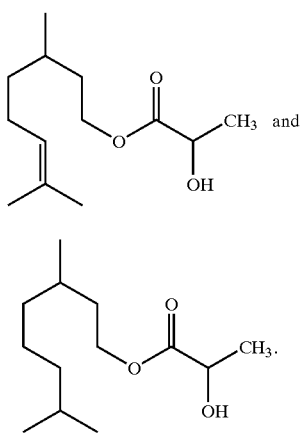

2. Citronellyl or dihydrocitronellyl lactate, optically active as regards the carbon in a position of the CH$_3$ group and of the ester function, in (R) or (S) form, of formula (Ia) or (I'a):

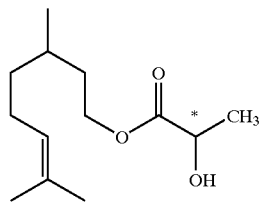

and

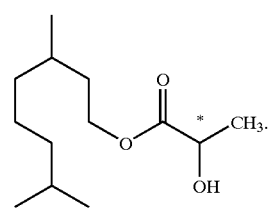

3. A process for the preparation of citronellyl lactate or dihydrocitronellyl lactate of formulae (I) and (I'):

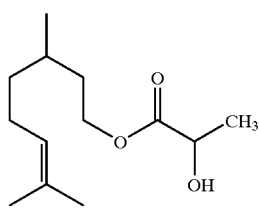

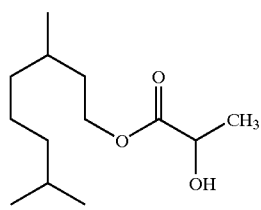

comprising the step of a):

reacting citronellol or dihydrocitronellol and a lactic acid, its salts or esters of formula (II):

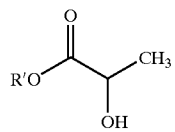

wherein: R' represents a hydrogen atom, an alkali-metal atom, an ammonium radical or a linear or branched alkyl radical having from 1 to 4 carbon atoms.

4. A process for the preparation of citronellyl lactate or dihydrocitronellyl lactate, optically active as regards the carbon in a position of the CH$_3$ group and of the ester function, of formulae (Ia) and (I'a):

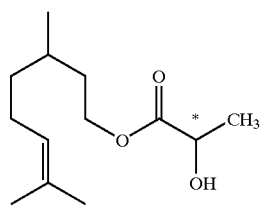
(Ia)

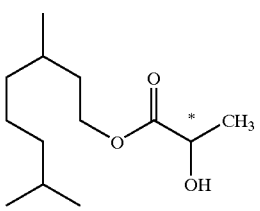
(I'a)

comprising the step of a):
reacting citronellol or dihydrocitronellol and a lactic acid, its salts or esters, optically active, of formula (IIa):

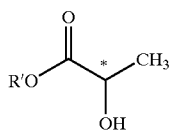
(IIa)

wherein: R' represents a hydrogen atom, an alkali-metal atom, an ammonium radical or a linear or branched alkyl radical having from 1 to 4 carbon atoms.

5. A process according to claim 3, wherein the compound of formula (II) is lactic acid, sodium lactate, potassium lactate, or methyl or ethyl esters of lactic acid.

6. A process according to claim 4, wherein the compound of formula (II) is lactic acid, sodium lactate, potassium lactate or methyl or ethyl esters of lactic acid.

7. A process according to claim 5, further comprising in step a) the presence of an organic solvent which forms an azeotrope with water.

8. A process according to claim 6, further comprising in step a) the presence of an organic solvent which forms an azeotrope with water.

9. A process according to claim 3, further comprising in step a) the reaction of the lactic acid or its salts with phosgene, diphosgene (trichloromethylchloroformate) or thionyl chloride in order to obtain, respectively, 5-methyl-1,3-dioxan-1,3-dione or propene-one-1 sulphite-1,2 with which the citronellol or the dihydrocitronellol is reacted.

10. A process according to claim 4, further comprising in step a) the reaction of the lactic acid or its salts with phosgene, diphosgene (trichloromethylchloroformate) or thionyl chloride in order to obtain, respectively, 5-methyl-1,3-dioxan-1,3-dione or propene-one-1 sulphite-1,2 with which the citronellol or the dihydrocitronellol is reacted.

11. A process according to claim 3, further comprising after step a): b) distilling the corresponding alcohol released by transesterification.

12. A process according to claim 4, further comprising after step a): b) distilling the corresponding alcohol released by transesterification.

13. A process according to claim 5, wherein the compound of formula (II) is (R)-lactic acid.

14. A process for the preparation of perfuming compositions, perfumed substances or perfumed finished products comprising the step of adding an effective perfuming quantity of at least one citronellyl lactate or dihydrocitronellyl lactate of formula (I) or (I'):

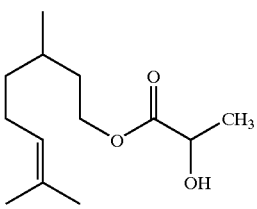
(I)

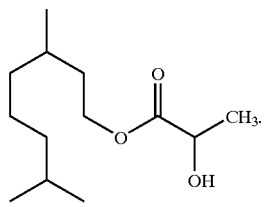
(I')

15. A process for obtaining perfuming compositions, perfumed substances or perfumed finished products, comprising the step of adding an effective quantity of at least one citronellyl lactate or dihydrocitronellyl lactate, optically active as regards the carbon in a position of the $CH_3$ group and of the ester function, of formula (Ia) or (I'a):

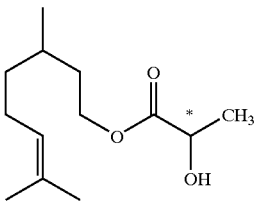
(Ia)

and

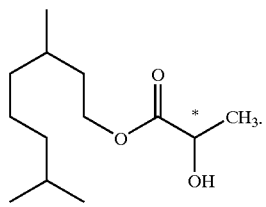
(I'a)

16. Perfuming compositions, perfumed products and substances comprising, as active principle having an influence on the smell, an effective quantity of at least one citronellyl lactate or dihydrocitronellyl lactate of formula (I) or (I') as defined in claim 2.

17. Perfuming compositions, perfumed products and substances comprising, as active principle having an influence on the smell, an effective quantity of at least one citronellyl lactate or dihydrocitronellyl lactate, optically active as regards the carbon in a position of the $CH_3$ group and of the ester function, of formula (Ia) or (I'a) as defined in claim 3.

18. Perfumed article according to claim 16, in the form of perfume, toilet water, after-shave lotions, perfumes, soaps, bath gels, shower gels, deodorant products, antiperspirant products, shampoos, hair product, talcs, powders, ambient-air deodorants, maintenance product, detergent compositions, or textile-softening compositions.

19. Perfumed article according to claim 17, in the form of perfume, toilet water, after-shave lotions, perfumes, soaps, bath gels, shower gels, deodorant products, antiperspirant products, shampoos, hair product, talcs, powders, ambient-air deodorants, maintenance product, detergent compositions, or textile-softening compositions.

20. A process according to claim 14, wherein the product of formula (I) gives a flowery character.

21. A process according to claim 15, wherein the optically active citronellyl lactate (R) of formula (Ia) gives a flowery character of lily of the valley.

22. A process according to claim 15, wherein the optically active citronellyl lactate (S) of formula (Ia) gives a flowery honeysuckle character.

23. A process according to claim 15, wherein the optically active dihydrocitronellyl lactate (R) of formula (I'a) gives a citronella-like, grassy, woody character.

24. A process according to claim 15, wherein the optically active dihydrocitronellyl lactate (S) of formula (I'a) gives a rosy, woody, lemony character.

* * * * *